United States Patent
Seibel

(10) Patent No.: US 6,283,913 B1
(45) Date of Patent: Sep. 4, 2001

(54) 3-DIMENSIONAL LID SPECULUM AND METHOD FOR USE

(76) Inventor: Barry S. Seibel, 956 Chattanooga Ave., Pacific Palisades, CA (US) 90272

(*) Notice: Subject to any disclaimer, the term of this patent is extended or adjusted under 35 U.S.C. 154(b) by 0 days.

(21) Appl. No.: 09/545,938

(22) Filed: Apr. 10, 2000

Related U.S. Application Data

(60) Provisional application No. 60/128,506, filed on Apr. 9, 1999.

(51) Int. Cl.$^7$ ........................................... A61B 1/32
(52) U.S. Cl. ..................... 600/236; 600/219; 600/225
(58) Field of Search .................................. 600/236, 235, 600/219, 225, 227, 231

(56) References Cited

U.S. PATENT DOCUMENTS

| | | | |
|---|---|---|---|
| 2,438,646 | * | 3/1948 | Pulliam ........................... 600/236 X |
| 2,702,540 | * | 2/1955 | Debeh . |
| 4,321,916 | * | 3/1982 | McKee . |
| 5,341,798 | * | 8/1994 | Grounauer . |
| 5,433,190 | * | 7/1995 | Sunalp ................................. 600/236 |
| 5,618,261 | * | 4/1997 | Nevyas ................................ 600/236 |

FOREIGN PATENT DOCUMENTS

| | | | |
|---|---|---|---|
| 114051 | * | 3/1918 | (GB) ................................... 600/236 |
| 1076081 | * | 2/1984 | (SU) ................................... 600/219 |

* cited by examiner

Primary Examiner—Jeffrey A. Smith
(74) Attorney, Agent, or Firm—Irell & Manella, LLP

(57) ABSTRACT

A lid speculum that operates in an anatomically correct manner. The speculum has a first blade and a second blade that can pivot about an axis of rotation. The speculum is constructed so that the axis of rotation is essentially parallel with and posterior to a line that intersects a medial canthi and lateral canthi of an eye. With such an arrangement the blades will move in a radial manner that corresponds to the shape of the globe. This movement tends to lessen kinked pressure points in the eyelid.

12 Claims, 6 Drawing Sheets

3-DIMENSIONAL LID SPECULUM AND METHOD FOR USE

CROSS-REFERENCE TO RELATED APPLICATION

The present application claims benefit of U.S. Provisional Application No. 60/128,506, filed Apr. 9, 1999.

BACKGROUND OF THE INVENTION

1. Field of the Invention

The present invention relates to a lid speculum that can be used to retract an eyelid of an eye.

2. Prior Art

Lid speculums are typically used to retract an eyelid when performing an ophthalmic procedure. For example, the eyelid is retracted when performing a phacoemulsification or LASIK procedure. Unfortunately, lid speculums of the prior art do not operate in an anatomically correct manner. Prior art speculums tend to create pressure points that cause patient discomfort.

FIGS. 1a–j show a conventional lid speculum 1 retracting an eyelid E. The lid speculum 1 has a pair of blades 2 that pivot about a pivot axis 3. In order to have the blades 2 essentially parallel when opened, the speculum is placed on the patient in a manner that creates an anatomically incorrect angle, as shown in FIGS. 1b and 1d. This results in a kinked and uncomfortable pressure point 4 in both the upper and lower eyelids.

The blades 2 maintain a constant two-dimensional plane of orientation as they are opened, pulling directly from each other, as indicated by the arrows in FIG. 1c, instead of following the contour of the globe. The blades 2 are parallel when initially open but then become oblique and create a pressure point 5 at the kinked tarsal plate. It would be desirable to provide a lid speculum that would operate in a more anatomically correct manner than speculums of the prior art.

BRIEF SUMMARY OF THE INVENTION

One embodiment of the present invention is a lid speculum that has a pair of blades that rotate about an axis of rotation. The axis of rotation is essentially parallel with a line that intersects the medial canthi and the lateral canthi of an eye.

DETAILED DESCRIPTION OF THE PREFERRED EMBODIMENT

Figure 1A:
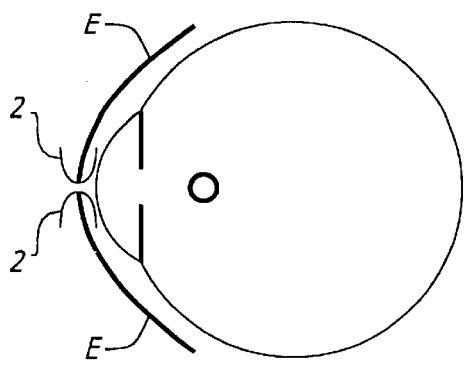
FIGS. 1a–j are illustrations showing eyelids being retracted by a lid speculum of the prior art.
Figure 1B:
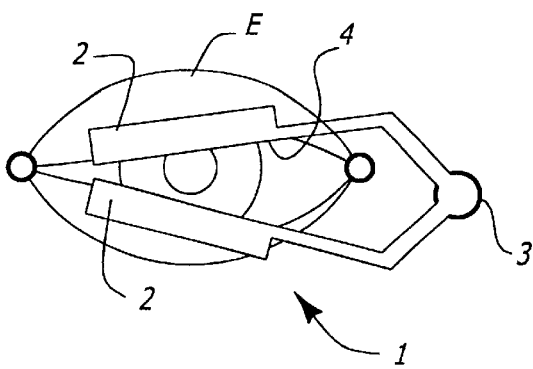
Figure 1C:
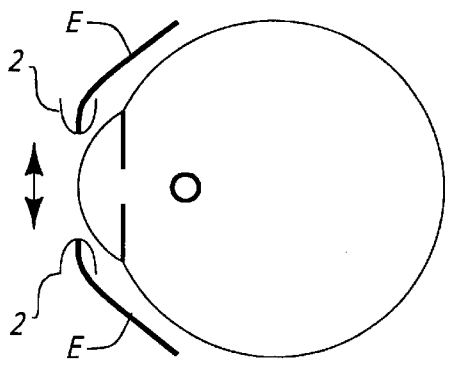
Figure 1D:
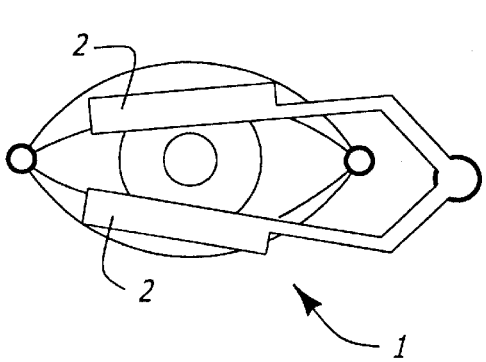

In general, the present invention is a lid speculum that operates in an anatomically correct manner. The speculum has a first blade and a second blade that can pivot about an axis of rotation. The speculum is constructed so that the axis of rotation is essentially parallel with and posterior to a line that intersects a medial canthi and lateral canthi of an eye. With such an arrangement the blades will move in a radial manner that corresponds to the shape of the globe. This movement tends to lessen kinked pressure points in the eyelid.

Referring to the drawings more particularly by reference numbers, FIGS. 2a–f show an embodiment of a lid speculum 10 of the present invention. The speculum 10 may have a first blade 12 that can retract a top eyelid 14 and a second blade 16 that can retract a bottom eyelid 18 located adjacent to a globe 20.

The first 12 and second 16 blades pivot about an axis of rotation R that is essentially parallel with and posterior to a line L that intersects the lateral canthi 22 and the medial canthi 24 of the eye. Therefore the blades 12 and 16 pivot in the same manner as the eyelids 14 and 18 to provide an anatomically correct lid speculum 10, as indicated by the arrows. The movement of the blades is similar to a visor of a helmet. A speculum 10 that operates in an anatomically correct manner reduces the likelihood of pressure points and patient discomfort even when the eyelids 14 and 18 are fully retracted.

Figure 1E:
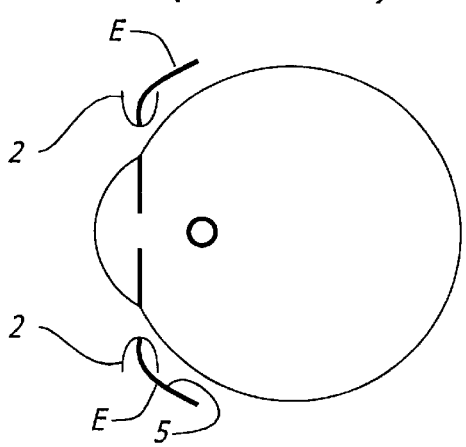
Figure 1F:
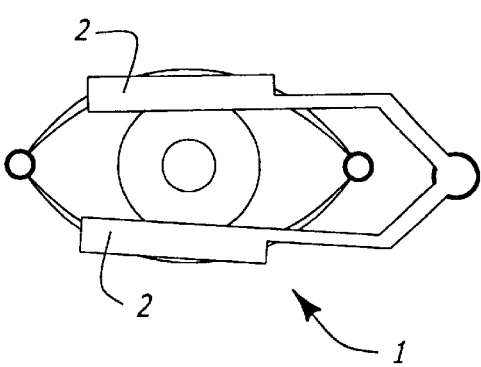
Figure 1G:
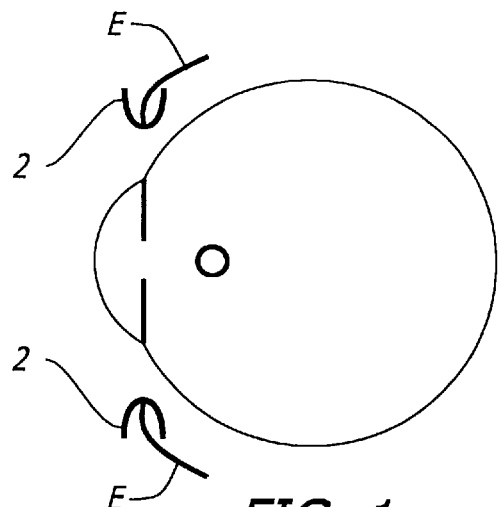
Figure 1H:
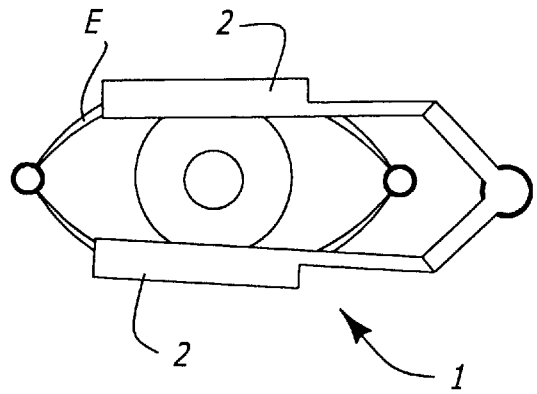
Figure 1I:
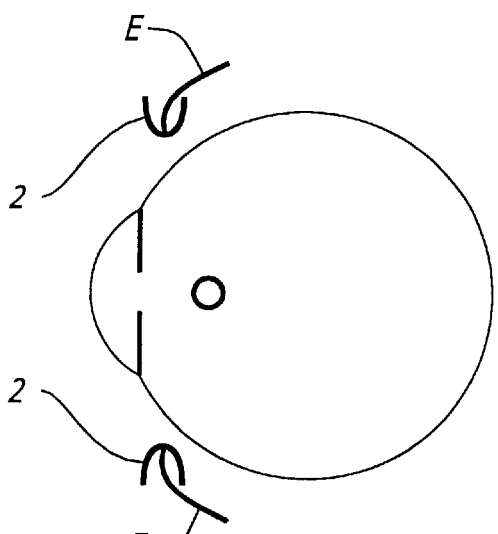
Figure 1J:
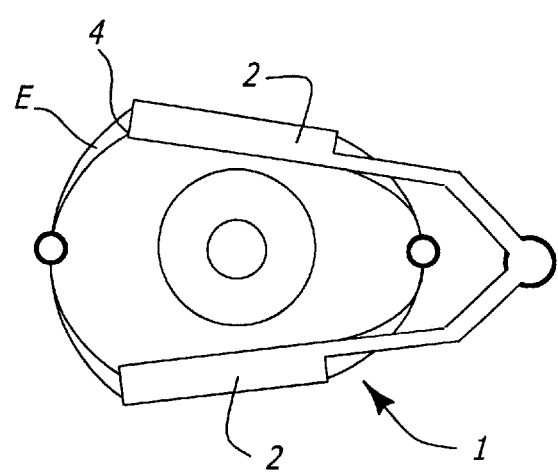
Figure 2A:
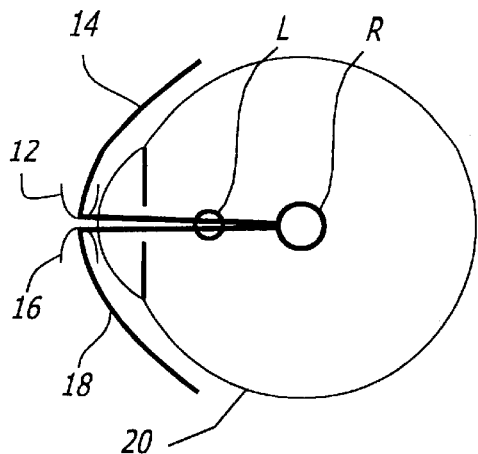
FIGS. 2a–f are illustrations showing eyelids being retracted by a lid speculum of the present invention.
Figure 2B:
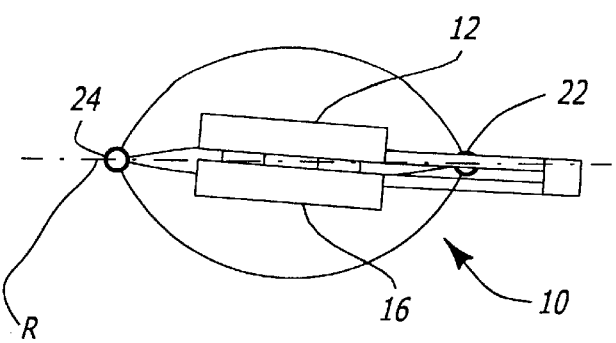
Figure 2C:
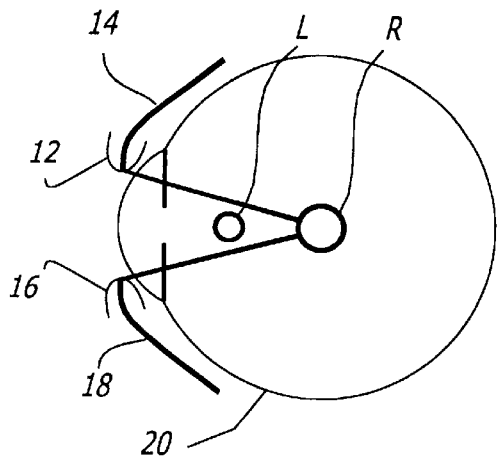
Figure 2D:
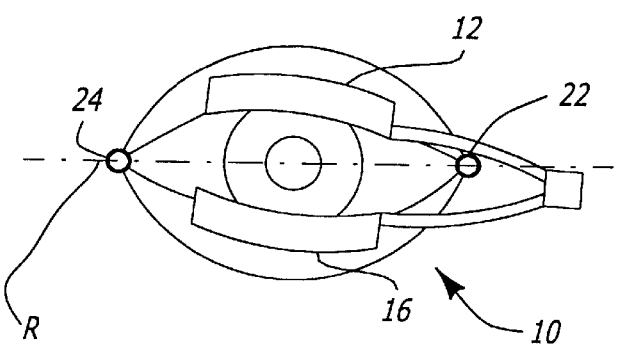
Figure 2E:
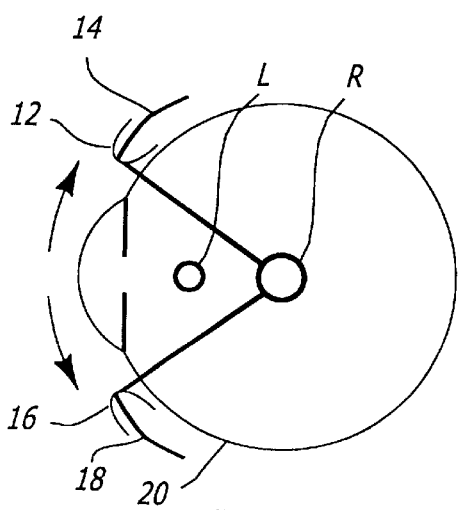
Figure 2F:
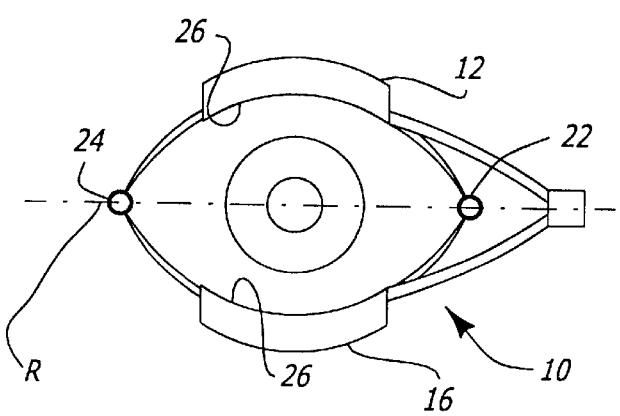

The first 12 and second 16 blades may each have a first curved surface 26 that provides additional space for another medical device (not shown) to be placed on the eye. For example, it may be desirable to place a circular shaped microkeratome onto the eye to perform a LASIK procedure. The curved surface 26 is more accommodating to a microkeratome than a straight speculum blade, as shown in FIG. 2f. Straight speculum blades require a greater retractions of the eyelid and more discomfort to the patient to load a microkeratome. Additionally, when combined with the anatomically correct movement of the speculum, the curved blades change orientation and greatly reduce the pressure point 5 shown in FIG. 1e, see FIG. 2e.

Figure 3A:
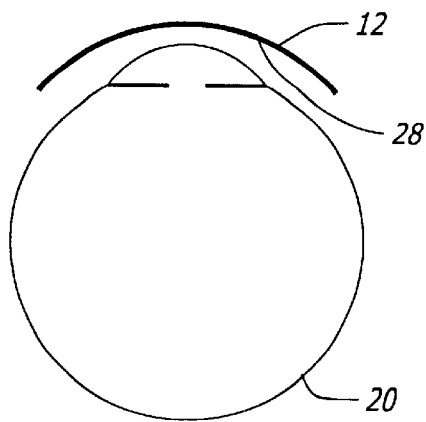
FIGS. 3a–c are illustrations showing a top view of a blade moving to a retracted position.
Figure 3B:
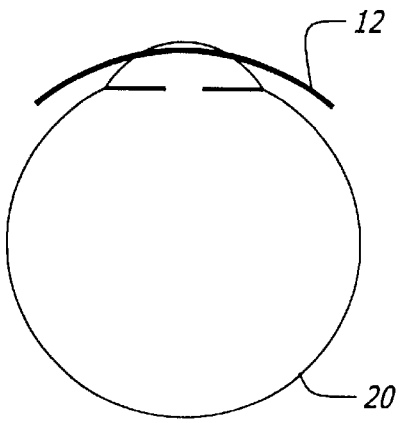
Figure 3C:
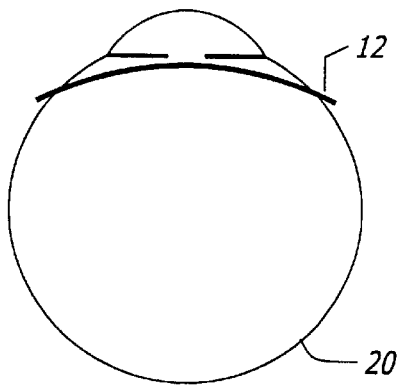

Referring to FIGS. 3a–c, the blades 12 may have a second curved surface 28 that conforms with the natural contour of the cornea 20, just like the natural movement of an eyelid. The FIGS. 3a–c show one of the blades moving from a closed position to a retracted position. Because of the second curved surface 28 the blade 12 appears to straighten out when moving across the sphere-like cornea 20. This relative movement of the blade 12 reduces eyelid stretching and the amount of patient discomfort.

Figure 4:
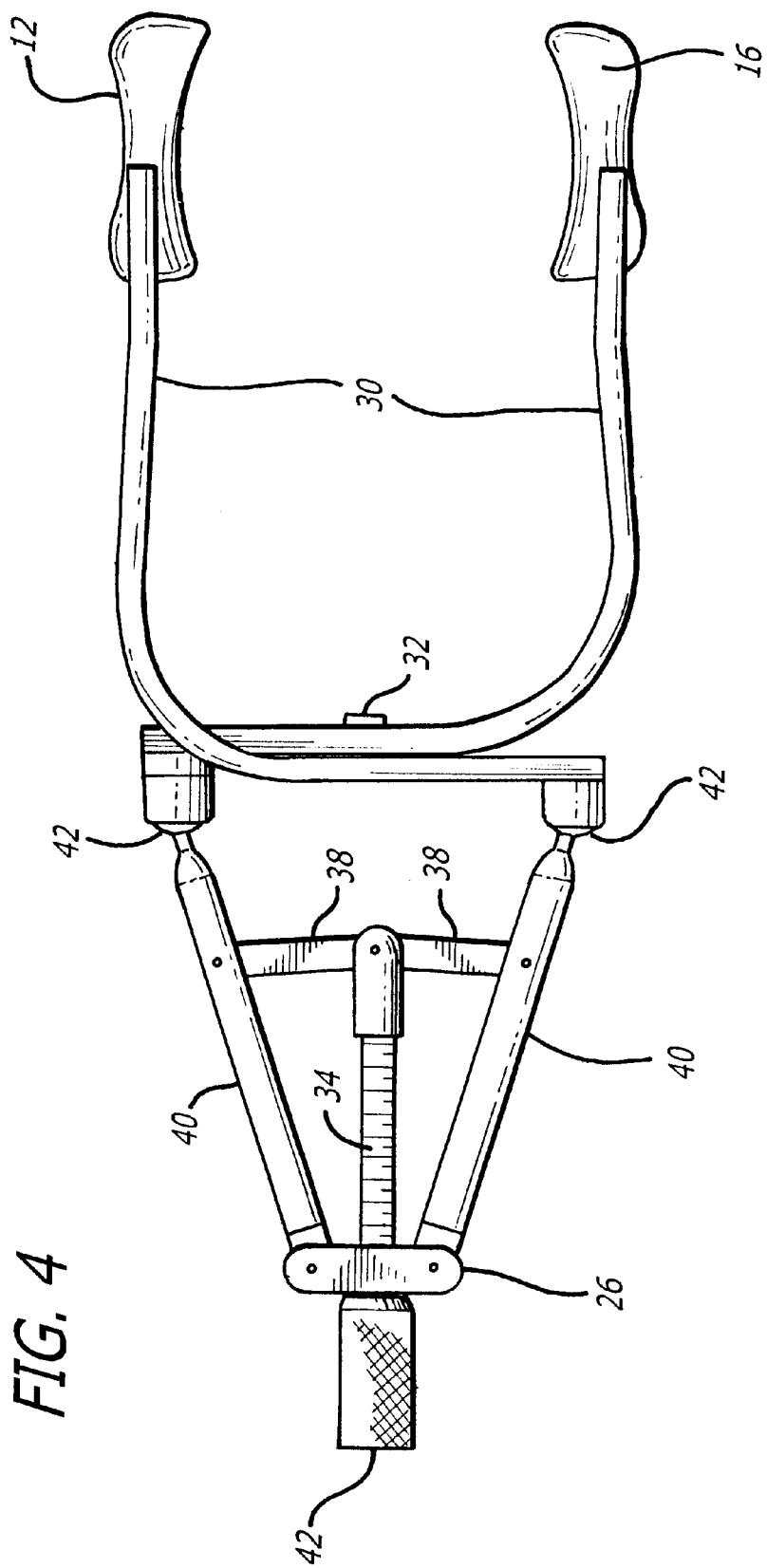
FIG. 4 is a top view of an embodiment of a lid speculum in a retracted position.
Figure 5:
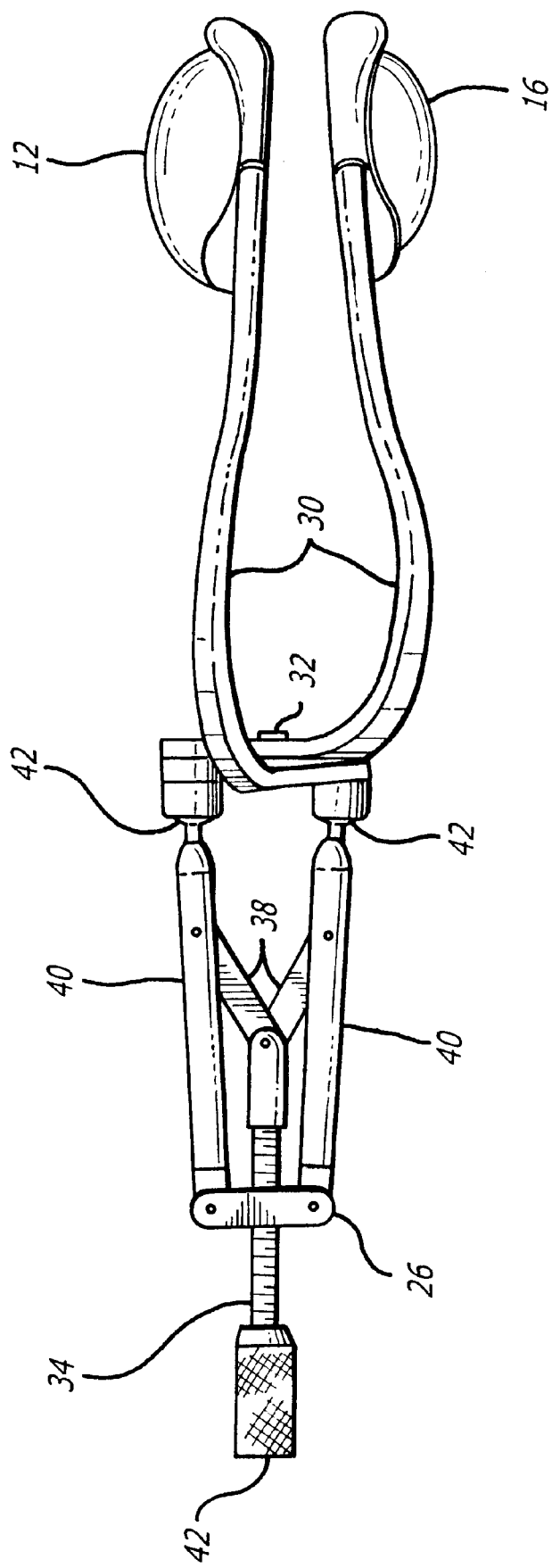
FIG. 5 is a bottom view of the lid speculum in a closed position.
Figure 4:
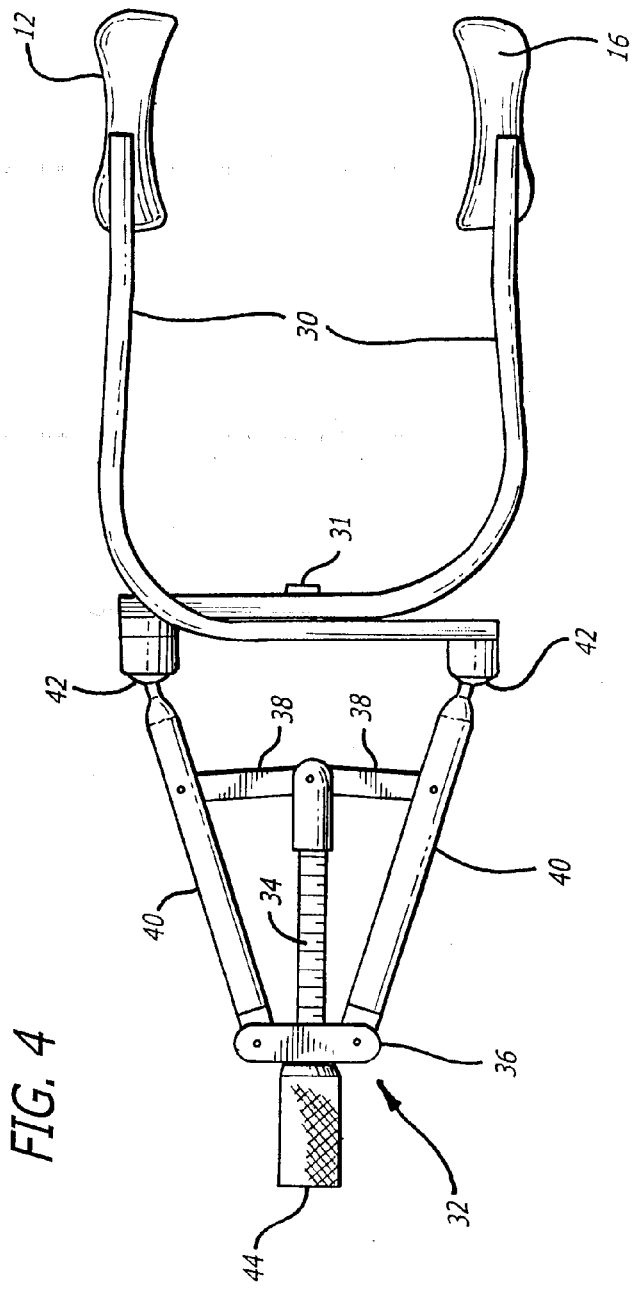
Figure 5:
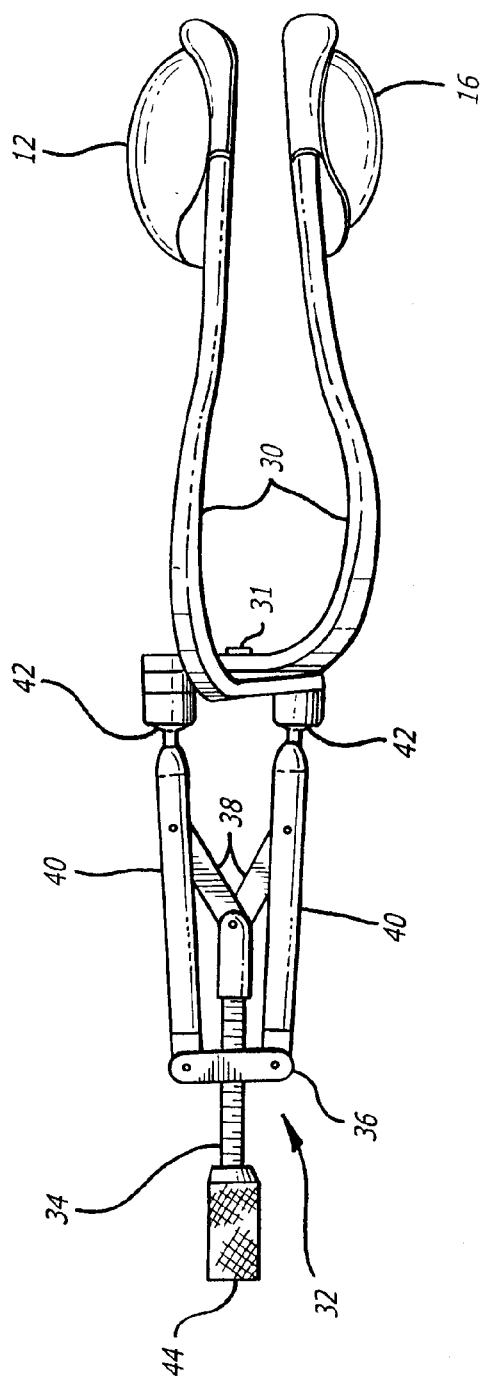

FIGS. 4 and 5 show an embodiment of the lid speculum 10. The speculum 10 includes the first blade 12 and the second blade 16. The blades 12 and 16 are attached to a pair of arms 30 that are connected by a pivot pin 31. The arms 30 and corresponding blades 12 and 16 are moved by a manipulator 32.

The manipulator 32 may include a lead screw 34 that can turn through a threaded aperture (not shown) of a base bar 36. The lead screw 34 is pivotally attached to a pair of inner linkage arms 38. The inner linkage arms 38 are pivotally connected to a pair of outer linkage arms 40. The outer linkage arms 40 are coupled to the blade arms 30 by a pair of ball joints 42. The ball joints on the actuating mechanism allow maximum surgeon ergonomics in allowing operation of the speculum throughout a wide range of orientation of the actuating knob. However, once the desired opening is obtained, the mechanism simply falls down to the side of the patient's head where it is unobtrusive relative to prior art screw mechanisms, which are fixed and would therefore either protrude out to the side or else be difficult to operate if they were fixed to angle down next to the patient's head.

Although a ball joint is described, it is to be understood that other types of joints or joint assemblies may be used to provide multiple degrees of freedom.

The lead screw 34 is attached to a head 44 that can be rotated by a surgeon. Rotating the head 44 translates the lead screw 34 and moves the arms 30, 38 and 40 to either retract or close the blades 12 and 16. Although a manually actuated head is shown and described, it is to be understood that the lead screw 34 may be rotated automatically through a motor or other device.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although the axis of rotation is shown posterior to the line L between the medial and lateral canthi, the rotational axis could be at line L or slightly anterior, superior, or inferior, to line L.

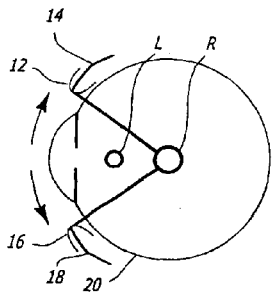

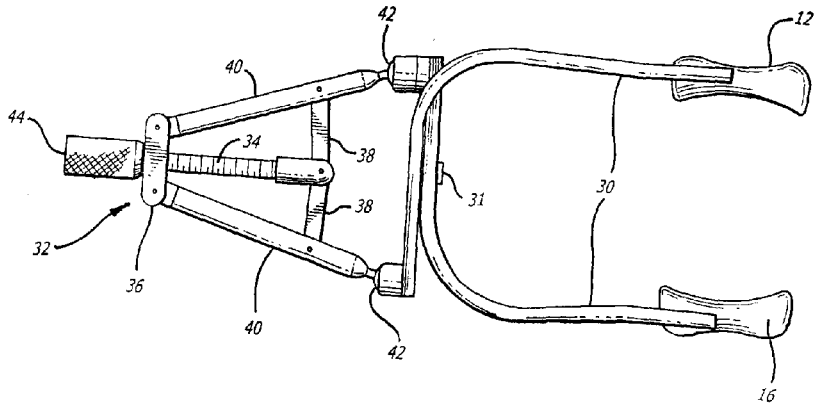

What is claimed is:

1. A lid speculum that can be used on an eye that has a medial canthi and a lateral canthi, comprising:
    a first blade that rotates about an axis of rotation that is essentially parallel with a line that intersects the medial canthi and the lateral canthi, said first blade having a proximal end attached to a pivot point and an unattached distal end;
    a second blade that pivots about the axis of rotation, said second blade having a proximal end attached to said pivot point and an unattached distal end; and,
    a manipulator that can be activated to pivot said first and second blades about said pivot point.

2. The lid speculum of claim 1, wherein said first and second blades each have a curved portion that conforms with the natural contour of the eye.

3. The lid speculum of claim 1, wherein said manipulator includes a lead screw that is connected to a linkage mechanism which is coupled to said first and second blades.

4. The lid speculum of claim 3, wherein said first and second blades are coupled to said linkage mechanism by a plurality of universal joints.

5. The lid speculum of claim 1, further comprising a pin that couples said first blade to said second blade.

6. A lid speculum comprising:
    a first blade;
    a second blade;
    a first arm attached to said first blade;
    a second arm attached to said second blade;
    a pivot pin attached to said first and second arms such that said first and second blades pivot about said pivot pin;
    a manipulator; and,
    a plurality of universal joints that couple said first and second arms to said manipulator.

7. The lid speculum of claim 6, wherein said manipulator includes a linkage mechanism coupled to said universal joints and a lead screw coupled to said linkage mechanism.

8. A method for retracting an eyelid of an eye that has a medial canthi and a lateral canthi, comprising;
    pivoting a first blade and a second blade about an axis of rotation that is essentially parallel with a line that intersects the medial canthi and the lateral canthi, and about a single pivot point by actuating a manipulator wherein the first and second blades each have unattached distal ends.

9. A lid speculum that can be used on an eye that has a medial canthi and a lateral canthi, comprising:
    a first blade that rotates about an axis of rotation that is essentially parallel with to a line that intersects the medial canthi and the lateral canthi;
    a second blade that pivots about the pivot axis; and,
    a manipulator that can pivot said first and second blades said manipulator includes a lead screw that is connected to a linkage mechanism which is coupled to said first and second blades.

10. The lid speculum of claim 9, wherein said first and second blades each have a curved portion that conforms with the natural contour of the eye.

11. The lid speculum of claim 10, wherein said first and second blades are coupled to said linkage mechanism by a plurality of universal joints.

12. The lid speculum of claim 9, further comprising a pin that couples said first blade to said second blade.

* * * * *

UNITED STATES PATENT AND TRADEMARK OFFICE
CERTIFICATE OF CORRECTION

PATENT NO. : 6,283,913 B1
DATED : September 4, 2001
INVENTOR(S) : Barry S. Seibel It is certified that error appears in the above-identified patent and that said Letters Patent is hereby corrected as shown below:

<u>Title page,</u>
The title page, should be deleted to appear as per attached title page.
The sheets of drawings, consisting of Figures 4-5 should be deleted to appear as per attached sheets.

<u>Drawings,</u>
Figure 4, please replace number "32" with number -- 31 --.
Figure 4, please replace number "26" with number -- 36 --.
Figure 4, please replace number "42" with number -- 44 --.
Figure 4, please add number -- 32 --.

Figure 5, please replace number "32" with number -- 31 --.
Figure 5, please replace number "26" with number -- 36 --.
Figure 5, please replace number "42" with number -- 44 --.
Figure 5, please add number -- 32 --.

<u>Column 1</u>
Line 59, please replace "bottom" with -- top --.

Signed and Sealed this

Thirteenth Day of August, 2002

*Attest:*

*Attesting Officer*

JAMES E. ROGAN
*Director of the United States Patent and Trademark Office*

United States Patent
Seibel

(10) Patent No.: US 6,283,913 B1
(45) Date of Patent: Sep. 4, 2001

(54) 3-DIMENSIONAL LID SPECULUM AND METHOD FOR USE

(76) Inventor: Barry S. Seibel, 956 Chattanooga Ave., Pacific Palisades, CA (US) 90272

(*) Notice: Subject to any disclaimer, the term of this patent is extended or adjusted under 35 U.S.C. 154(b) by 0 days.

(21) Appl. No.: 09/545,938

(22) Filed: Apr. 10, 2000

Related U.S. Application Data

(60) Provisional application No. 60/128,506, filed on Apr. 9, 1999.

(51) Int. Cl.[7] ............................................. A61B 1/32
(52) U.S. Cl. ........................... 600/236; 600/219; 600/225
(58) Field of Search ................................. 600/236, 235, 600/219, 225, 227, 231

(56) References Cited

U.S. PATENT DOCUMENTS

| | | | |
|---|---|---|---|
| 2,438,646 | * | 3/1948 | Pulliam .................. 600/236 X |
| 2,702,540 | * | 2/1955 | Debeh . |
| 4,321,916 | * | 3/1982 | McKee . |
| 5,341,798 | * | 8/1994 | Grounauer . |
| 5,433,190 | * | 7/1995 | Sunalp .................... 600/236 |
| 5,618,261 | * | 4/1997 | Nevyas .................... 600/236 |

FOREIGN PATENT DOCUMENTS

| | | | |
|---|---|---|---|
| 114051 | * | 3/1918 | (GB) .................... 600/236 |
| 1076081 | * | 2/1984 | (SU) .................... 600/219 |

* cited by examiner

*Primary Examiner*—Jeffrey A. Smith
(74) *Attorney, Agent, or Firm*—Irell & Manella, LLP

(57) ABSTRACT

A lid speculum that operates in an anatomically correct manner. The speculum has a first blade and a second blade that can pivot about an axis of rotation. The speculum is constructed so that the axis of rotation is essentially parallel with and posterior to a line that intersects a medial canthi and lateral canthi of an eye. With such an arrangement the blades will move in a radial manner that corresponds to the shape of the globe. This movement tends to lessen kinked pressure points in the eyelid.

12 Claims, 6 Drawing Sheets